(12) United States Patent
Duncan et al.

(10) Patent No.: US 6,372,205 B1
(45) Date of Patent: Apr. 16, 2002

(54) PHARMACEUTICAL COMPOSITIONS CONTAINING ANTIBODY-ENZYME CONJUGATES IN COMBINATION WITH PRODRUGS

(75) Inventors: Ruth Duncan, London (GB); Ronit Satchi-Fainaro, Ramat Aviv (IL)

(73) Assignee: The School of Pharmacy, University of London (GB)

( * ) Notice: Subject to any disclaimer, the term of this patent is extended or adjusted under 35 U.S.C. 154(b) by 0 days.

(21) Appl. No.: 09/445,732

(22) PCT Filed: Jun. 11, 1998

(86) PCT No.: PCT/GB98/01700

§ 371 Date: May 22, 2000

§ 102(e) Date: May 22, 2000

(87) PCT Pub. No.: WO98/56425

PCT Pub. Date: Dec. 17, 1998

(30) Foreign Application Priority Data

Jun. 11, 1997 (EP) .............................................. 97304070

(51) Int. Cl.⁷ ......................... A61K 31/74; A61K 47/48
(52) U.S. Cl. ................. 424/78.17; 424/78.08; 424/94.1
(58) Field of Search ........................... 424/78.08, 78.17, 424/94.1

(56) References Cited

PUBLICATIONS

Chem. AG. 1995:294200 CZ278551 1994.*
Chem. AG . 127: 126464 R.Satchi et al 1997.*
Krinick, N.L. (1992) "Combination polymeric drugs as anticancer agents" *Diss Abstr Int* 52(12):6525, abstract No. XP002049282.
Nichifor, M. et al. (1996) "Macromolecular prodrugs of 5–fluorouracil. 2: Enzymatic degradation" *Journal of Controlled Release* 39(1):79–92, abstract No. XP002040091.
Nichifor, M. et al. (1997) "Polymeric prodrugs of 5–fluorouracil" *Journal of Controlled Release* 48:165–178, abstract No. XP002049283.

* cited by examiner

*Primary Examiner*—Thurman K. Page
*Assistant Examiner*—Liliana Di Nola-Baron
(74) *Attorney, Agent, or Firm*—Saliwanchik, Lloyd & Saliwanchik

(57) ABSTRACT

Prodrugs which can be activated by enzymes, are formulated for sequential administration, with enzyme conjugates. Either or each component comprises a polymeric carrier which allows it to be directed preferentially to the target tissue. A new polymer-prodrug conjugate is cleavable by cathepsin-B or othe invention is of particular utility for targeting solid tumours.

39 Claims, 9 Drawing Sheets

PHARMACEUTICAL COMPOSITIONS CONTAINING ANTIBODY-ENZYME CONJUGATES IN COMBINATION WITH PRODRUGS

FIELD OF THE INVENTION

The present invention relates to compositions and kits for use in enzyme-prodrug therapy, in which the enzyme is conjugated to a carrier.

BACKGROUND OF THE INVENTION

The chemotherapy of neoplastic disease is often compromised by adverse systemic toxicity which limits the dose of drug that can be administered, or is limited by the appearance of multidrug resistance. Various strategies have been explored to improve drug targeting and to increase drug concentration in the tumour to a level that should overcome clinically relevant drug resistance.

Prodrugs have been used for many years in medicine to treat a variety of disorders. They can offer improved solubility, improved pharmacokinetics and tissue distribution, avoidance of unfavourable metabolism, selective organ effects and specific tumour toxicity. In order to use prodrugs as anticancer agents, the tumour must have a high level of the enzyme that activates the prodrug, or a foreign enzyme must be delivered, and no activating enzyme must be present in normal tissues. The prodrug must be innocuous and pharmacodynamically inert and be a substrate for the enzyme with favourable Km and Vmax values.

The concepts of Antibody Directed Enzyme Prodrug Therapy (ADEPT) (refs. 1,2) and Gene/Viral Directed Enzyme Prodrug Therapy (G/VDEPT) (ref. 3) using either antibody conjugates or a retroviral vector to deliver an enzyme to a tumour are already well established. In ADEPT, a foreign enzyme which metabolises substrates not normally metabolised by mammalian cells is linked chemically to a tumour-specific or tumour-associated antibody; the antibody conjugate is injected intravenously and binds strongly to the tumour by recognising the tumour-associated antigen. In VDEPT, the retroviral vector is designed to carry a gene expressing a preselected enzyme that can be delivered selectively to tumour or be under the control of a tumour-specific promoter. The foreign enzyme is then used to activate a carefully designed low molecular weight prodrug. Animal models and pilot human studies have proven that it is possible to deliver selectively to a solid tumour an activating enzyme such as carboxypeptidase G2, penicillin amidase, β-lactamase, β-glucuronidase, cytosine deaminase, nitroreductase or alkaline phosphatase (refs. 4,5).

Both approaches have a number of inherent limitations. In the case of ADEPT, these include the immunogenicity of the antibody-enzyme conjugate, the need to tailor each conjugate to target antigen present on the tumour, the difficulty in optimisation of the dosing schedule, and the need to use a clearing antibody in the case of ADEPT (ref. 6). In the case of VDEPT, there are the inherent dangers associated with a viral vector, the potential lack of specificity of enzyme expression in the tumour due to problems of delivering the gene specifically to cancer cells, and the difficulty of evaluating the duration and reproducibility of enzyme expression on a patient basis, leading to difficulties in optimising the schedule of prodrug follow-up.

In recent years, there has been a great deal of investigation of polymers as carriers of anticancer drugs (reviewed in ref. 7). The basis for much of this work is that attachment of toxic drugs to high molecular weight carriers can lead to reduction in systemic toxicity, longer retention time in the body, alterations in biological distribution, improvements in therapeutic efficacy and site-specific passive capture through the enhanced permeability and retention (EPR) effect. The EPR effect results from enhanced permeability of macromolecules or small particles within the tumour neovasculature, due to the leakiness of its discontinuous endothelium. In addition to the tumour angiogenesis (hypervasculature) and irregular and incompleteness of vascular networks, the attendant lack of lymphatic drainage promotes accumulation of macromolecules that extravasate (ref. 8). This effect is observed in many solid tumours for macromolecular agents and lipids. The enhanced vascular permeability will support the great demand of nutrients and oxygen for the rapid growth of the tumour. Unless specifically addressed for tumour cell uptake by receptor-medicated endocytosis, polymers entering the intratumoural environment are taken up relatively slowly by fluid-phase pinocytosis.

Many polymer-based anticancer agents have now entered the clinic or are passing through clinical trials; each has proven the concept compared to the native drug. For instance, N-(2-hydroxypropyl)methacrylamide (HPMA) copolymer-doxorubicin conjugates have already shown promise in early clinical trial (refs. 9,10). Moreover, residual HPMA copolymer conjugate which does not permeate in to the tumour but remains in the circulation is rapidly excreted, giving a high tumour:blood ratio (ref. 11).

In most cases, release of active anticancer drug from the polymer support is mediated by simple aqueous hydrolysis or by proteolytic or esterase enzymes (refs. 12,13). Since the conditions for these reactions are not necessarily confined to tumour tissues, some non-specific drug release is inevitable.

Conjugation of water-soluble polymers to pharmacologically-active proteins such as enzymes, toxins, immunoglobulins, cytoxins or allergens can be used to reduce the proteolytic degradation of such proteins, improve their biological efficacy and prolong plasma elimination, as well as reduce protein immunogenicity. For instance, an HPMA copolymer-asparaginase conjugate has been used to treat leukaemia. The conjugation of the enzyme to the polymer has been shown to increase the circulation time of the enzyme, where its activity in depriving leukaemic cells of asparagine is useful.

SUMMARY OF THE INVENTION

According to the present invention, a product or kit comprises two components, i.e. two pharmaceutical compositions that are arranged or otherwise adapted for sequential administration to a human or animal. The first component is an enzyme conjugate, e.g. a composition that comprises a pharmaceutically-acceptable excipient and an enzyme conjugate. The enzyme conjugate may consist of an enzyme covalently bound to a polymeric or other carrier such that the enzyme conjugate retains its enzyme activity. The second component is a prodrug, e.g. a composition that comprises a pharmaceutically-acceptable excipient and a prodrug. The prodrug is typically substantially inactive (in terms of drug activity) but capable of being activated by the enzyme.

It is to be noted that unless the context specifically refers to the order of administration of the product, reference herein to "first" and "second" compositions does not imply any specific order of administration.

The two components of the kit are used in a treatment regimen similar to ADEPT, except that the enzyme conjugate is administered in place of the antibody-enzyme conjugate. One significant difference is that the two components can be administered, in use of the present invention, in either order. For instance, prodrug-containing composition may be given first. The present invention can avoid the problems with ADEPT, resulting from the immunogenicity of the antibody-enzyme conjugate. Furthermore, although a polymer carrier is not specifically targeted to antigenic sites of the tumour cell surface, it is nevertheless expected to preferentially accumulate in solid tumours through the EPR effect. It has been observed that ADEPT is surprisingly non-specific in vivo, and it is believed that the polymerenzyme conjugate is likely to exhibit preferential accumulation as significant as that exhibited in ADEPT.

DESCRIPTION OF THE INVENTION

Figure 1:
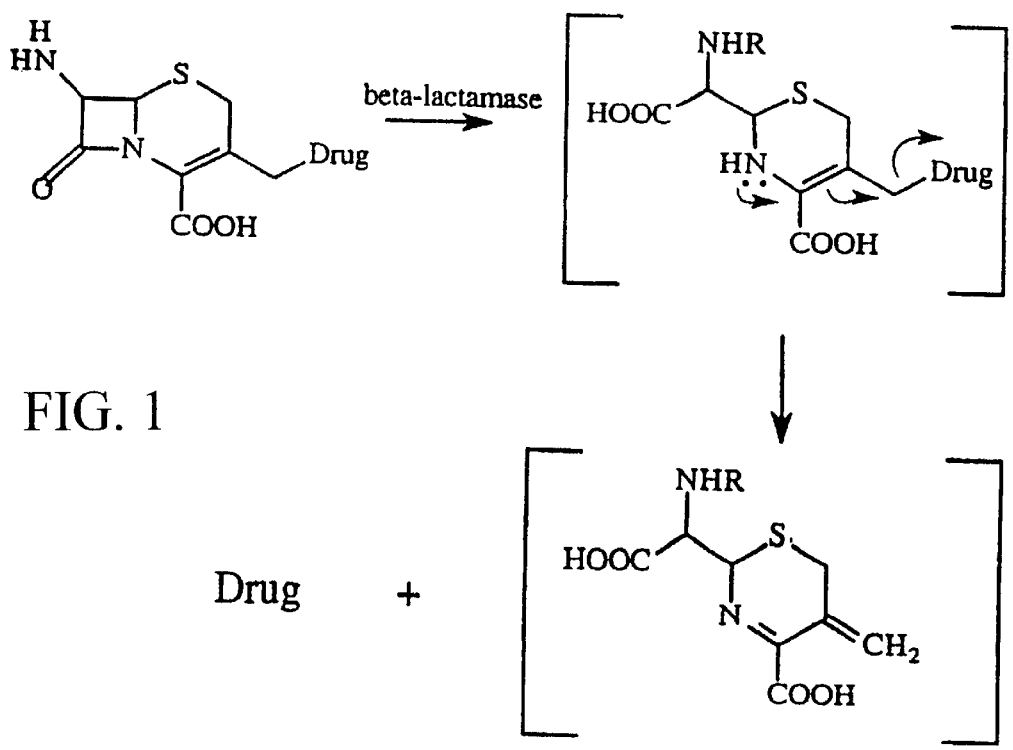
FIG. 1 shows the reaction mechanism of drug release from cephalosporin-linked prodrug by β-lactamase.

It is preferred that the molecular weight of the enzyme conjugate should be tailored to optimise the accumulation of the conjugate in the tumour. Thus the molecular weight should be sufficiently high that the conjugate does not pass through normal endothelium, but passes into the tumour through the leaky neovasculature and is accumulated by resisting removal therefrom. The molecular weight should be sufficiently low, however, for removal of residual non-tumour-accumulated conjugate through the kidneys. The total molecular weight of the conjugate should preferably be less than 1000 kD, more preferably less that 100 kD, and is preferably at least 20 kD.

The carrier of the enzyme conjugate is preferably a polymer, e.g. a water-soluble polymer to which a covalent bond may be formed with the enzyme. The bond between the polymer and the enzyme should allow retention of the enzyme's activity for the conjugate. The polymer may thus be bound through a spacer group allowing a distance between the polymer backbone and the enzyme, avoiding steric hindrance of the enzyme's active site. To avoid degradation, it may be preferred to use a polymer having a molecular weight of at least 30 kD.

In the enzyme conjugate, each enzyme molecule may be bound to a molecule of polymer through one or more links, preferably through a single covalent link. Furthermore, each polymer molecule may on average have fewer than one enzyme molecule bound to it. Preferably, however, the average number of enzyme molecules bound to a polymer molecule is at least one, more preferably 1 to 5. The preferred ratio depends upon the molecular weight of the enzyme, the molecular weight of the polymer and the optimum total molecular weight of the conjugate for accumulation of the conjugate in a tumour by the EPR effect.

Suitable polymers which have been used as carriers and of which conjugates appear to accumulate by the EPR effect, include polyethylene glycol, ethylene glycol copolymers, dextrin, polymers and copolymers of hydroxylalkyl (meth) acrylamide, for instance hydroxypropyl methacrylamide, and copolymers of styrene and maleic anhydride. Other polymers which may be used include polygalacturonic acid, copolymers of hydroxyalkyl (meth)acrylate, for instance N-phenylpyrrolidone, poly(L-glutamic acid hydroxyethyl-L-glutamine), poly(α-malic acid), polyaspartic acid-PEG copolymers, poly-L-lysine and copolymers of polyethyleneimine.

Whilst the enzyme-polymer conjugate may rely for its localisation at a solid tumour primarily upon EPR, it may be desirable to attach ligands allowing active targeting. For instance, it may be desirable to attach galactose ligands to target the conjugate to liver. Alternatively, melanocyte-stimulating hormone may be bound to the polymer, as a ligand for melanoma. If desired, an antibody may be joined to the polymer as a ligand, the antibody being directed to specific antigenic sites on the target tissue of interest. Whilst the use of such an antibody-polymer-enzyme conjugate may have some advantages over the antibody-enzyme conjugate used in the normal ADEPT system in terms of reduced immunogenicity, the present invention preferably avoids the use of active targeting ligands for the enzyme conjugate.

The enzyme conjugate includes functional enzyme. The conjugate preferably retains a significant level of enzyme activity. The level may be reduced as compared to the native enzyme, provided that significant useful activity is retained.

The prodrug used in the invention may be a relatively low molecular weight compound. The action of the enzyme on the prodrug may not significantly change the molecular weight of the compound. A useful summary of suitable prodrugs and the enzymes which activate the prodrugs is given in Table 1 of reference 5, a review article citing many references in which full details of the prodrugs and their use are described. Thus the enzyme may be selected from DT diaphorase, plasmin, carboxypeptidase G2, thymidine kinase (viral), cytosine deaminase, glucose oxidase, xanthine oxidase, carboxypeptidase A, α-galactosidase, β-glucosidase, azoreductase, γ-glutamyltransferase, β-glucuronidase, β-lactamase, alkaline phosphatase, aminopeptidase, penicillin amidase and nitroreductase.

One preferred enzyme is β-lactamase. The β-lactamases are a group of enzymes of varying specificity but all are capable of hydrolysing β-lactams to a substituted β-amino acid. Some act more readily on penicillins, while others have greater activity against cephalosporins. β-Lactamase activity is not endogenous to the mammalian systems and it is therefore subject to minimal interference from inhibitors, enzyme substrates or endogenous enzyme systems.

The synthesis of a range of cephalosporin derivatives of various mustards (ref. 14) and doxorubicin (ref. 15) has been described and these are relatively good substrates for the enzyme. The spacer between the polymer and the anticancer drug will contain a β-lactam ring in the form of a penicillin or cephalosporin. β-Lactamase cleaves the lactam ring and after a chemical rearrangement (shown in FIG. 1), the drug is produced. Many cytotoxic agents can be attached, provided that they have $NH_2$ or OH groups that can be substituted and thus act as prodrugs. The rate of the hydrolysis is measured in vitro by the change in absorbance.

Another preferred class of enzyme is protease/peptidase. Thiol-dependent proteases such as cathepsin B are particularly preferred.

The prodrug should be substantially inactive in terms drug activity. Thus the activated drug should preferably have an activity which is at least 100 times that of the prodrug, most preferably at least 1000 times the activity.

The drug may be selected from anti-tumour agents, antibiotics, antimetabolites, alkylating agents, alkaloids and microtubule inhibitors, and signal transduction modifiers. Preferably it is a cytotoxic agent, as the present invention has its primary utility in treatment of cancers. Thus the drug may be any known cytotoxic agent capable of being provided in the form of a prodrug for enzymic activation.

A suitable list of drugs and their prospective prodrugs, as well as the respective activating enzymes is given in reference 5, Table 1. Thus the drug may be selected from:

5-(Azurudub-1-yl)-4-dihydroxylamino-2-nitrobenzamide
Phenylenediamine mustard
Benzoic acid mustards (various)
Gangcyclovir triphosphate
Adenine arabinonucleoside triphosphate (araATP)
5-Fluorouracil
Hydrogen peroxide
Superoxide, hydrogen peroxide
Methotrexate
Cyanide
Phenylenediamine mustards (various)
Phenylendiamine mustard
Phenol Mustard
Anthracyclines e.g. Epirubicin, Doxorubicin and Daunorubicin
4-Desacetylvinblastine-3-carboxhydrazide
Nitrogen mustards (various)
Mitomycin alcohol
Etoposide
Palytoxin
Melphalan
5-(Aziridin-1-yl)-4-hydroxylamino-2-nitrobenzamide
Actinomycin D, mitomycin C
Taxanes, such as taxol and taxotere
Topoisomerase inhibitors such as camptothecin and topotecan.

Preferably the prodrug comprises a carrier to which the drug is conjugated. In some circumstances, it may be desirable for the enzymic activation of the prodrug not to be accompanied by release of activated drug from the polymer conjugate. Thus an activated drug-polymer conjugate may have polymer bound to drug moieties through linker moieties which are not cleaved by the enzyme, which allow the drug's activity to be retained. Alternatively, the activation of the prodrug through reaction of the enzyme may take place independently of cleavage of the drug moiety from the polymer conjugate, for instance through activity of a separate enzyme on the linker joining the drug moiety to the polymer.

It is, however, preferred for activation of a prodrug-polymer conjugate to occur by cleavage of a linker which is susceptible to cleavage by the enzyme.

Thus the linker may be a cephalosporin linker, which is cleaved by β-lactamase as described in reference 15. Preferably, however, the linker is a peptide moiety and the enzyme is a peptidase enzyme for which the peptide linker is the substrate.

In another embodiment of the invention, a prodrug comprises a conjugate of a polymer and a drug moiety joined together by a peptidyl linker, and an enzyme conjugate comprises an enzyme bound to a carrier moiety. The conjugate and the prodrug are components of a novel kit comprising two compositions, arranged for sequential administration, each containing one of the aforementioned conjugates.

The conjugate of polymer and drug moiety preferably has a molecular weight in the range 5 kD to 1000 kD, more preferably in the range 20 kD to 100 kD.

In this aspect of the invention, the enzyme conjugate may be a polymer-enzyme conjugate as used in the first aspect of the invention. It may also be an antibody-enzyme conjugate, for instance as used in ADEPT. Alternatively, the carrier may be another type of molecule capable of being actively targeted to desired target cells, or to which other proteins or components may specifically bind. For instance, the carrier may comprise a hormone or other specific moiety capable of specific binding to a carrier present in the circulation or to receptors on cell surfaces.

The enzyme used in this aspect of the invention is a peptidase enzyme capable of cleavage of the peptidyl linker of the prodrug conjugate. Cleavage of the linker preferably results in release of active drug. Alternatively, the enzymic reaction product may further react through subsequent steps to generate the active drug in situ. Preferably, the peptidase enzyme is a specific enzyme which cleaves specific peptide sequences only, and is not a non-specific peptidase.

The peptidyl linker comprises sufficient amino acid units to allow specific binding and cleavage by peptidase enzyme. Preferably, the linker is at least two amino acids long, more preferably at least three amino acids long, for instance four or more amino acids long.

In this aspect of the invention, again, the drug is preferably a cytotoxic drug. It is convenient for the peptidyl linker to be cleavable by enzymes which are present at relatively high levels in tumours as compared to tissue. A suitable enzyme is a thiol-dependent protease, for instance cathepsin-B. A specific substrate for cathepsin-B is a Gly-Phe-Leu-Gly linker.

Conjugation of polymer, linker and drug may be carried out using conventional chemical and biochemical techniques. For instance, pendant groups on the polymer may react with preformed peptide compounds and the polymer with peptide side-chains may subsequently be reacted with drug molecules. Alternatively, polymerisable peptide compounds are readily available and may be copolymerised with other monomers to form a polymer with pendant peptide groups, to which a drug compound may be reacted. The synthesis of the Gly-Phe-Leu-Gly-doxorubicin-HPMA conjugate is described in reference 16. It is shown to have reduced toxicity compared to free doxorubicin and improved anti-tumour activity in reference 17.

A further aspect of the present invention lies in the use of thiol-dependent proteases as the enzyme component of enzyme/prodrug therapy. A novel conjugate consists of a thiol-dependent protease covalently bound to a carrier, said conjugate retaining thiol-dependent protease activity. The enzyme is preferably cathepsin-B. The conjugate may be provided as part of a pharmaceutical composition or kit.

In this, third aspect of the invention, the carrier may, as for the second aspect, be an antibody or other active targeting component, but is preferably a polymer. Whilst it is preferred for a thiol-dependent protease-polymer conjugate not to be actively targeted, it may be possible to provide the polymer with active ligands such as antibodies and other specific binding components.

A product or kit comprises the novel conjugate and a prodrug comprising a drug bound to a carrier via a linker cleavable by the thiol-dependent protease.

In each aspect of the invention, the components may be used in a method of treatment. The treatment will be that associated with the drug. The amount of each component that should be administered will be dependent on the nature of the condition being treated and the particular drug that is used, as will be readily evident to one of ordinary skill in the art. Typical amounts and dosage regimes may be the same as or similar to those for related procedures, and can then be adjusted, if necessary.

In each aspect of the invention, the components may be administered to a patient in either order. It is preferred that the first composition to be administered is selected such that it is accumulated in tumour by EPR. Preferably, the component in the first composition to be administered is capable of being cleared normally from the circulation by the kidneys after a period of less than, for instance, 12 hours, preferably less than 6 hours (the circulation half-life). It is particularly convenient for the prodrug conjugate to be administered first, to achieve rapid accumulation in the tumour and subsequent clearance from the circulation of the potentially toxic prodrug by excretion through the kidneys. This is a significant improvement over the ADEPT system where the enzyme has to administered first.

Where the first administered component is not cleared from the circulation adequately, it may be appropriate to clear the component from the circulation by administering a clearing component. The first component to be administered may be provided with a ligand which is adapted for binding to an anti-ligand. This component can thus be cleared from the circulation by a second, clearing component which comprises an anti-ligand and a moiety which allows the clearing component to be adapted to be cleared from the circulation.

Preferably the first component to be administered in the novel method is the prodrug. It should therefore be adapted to optimise its EPR and hence tumour accumulation. Whilst the enzyme conjugate, which is administered second, in such preferred embodiments, is advantageously directed preferentially to the tumour, since the enzyme conjugate is generally substantially non-toxic, it is less important that the enzyme conjugate be adapted to optimise the EPR effect. The circulation time of the enzyme conjugate should be sufficiently long for activation at the desired site of substantially all the prodrug. The difference in time between the administration of the two compositions may be hours or even days. Controlling the molecular weight of the respective conjugates allows a degree of control of the optimum administration protocol.

An advantage of the third aspect of the present invention is that the prodrug, when preferentially accumulated in the tumour, will be activated intra- cellularly by endogenous thiol-dependent protease, present in increased levels inside the cells in tumours, and extracellularly by the thiol-dependent protease-carrier conjugate. This provides active drug outside cells which may be transported into cells which do not otherwise contain activated drug.

Figure 2:
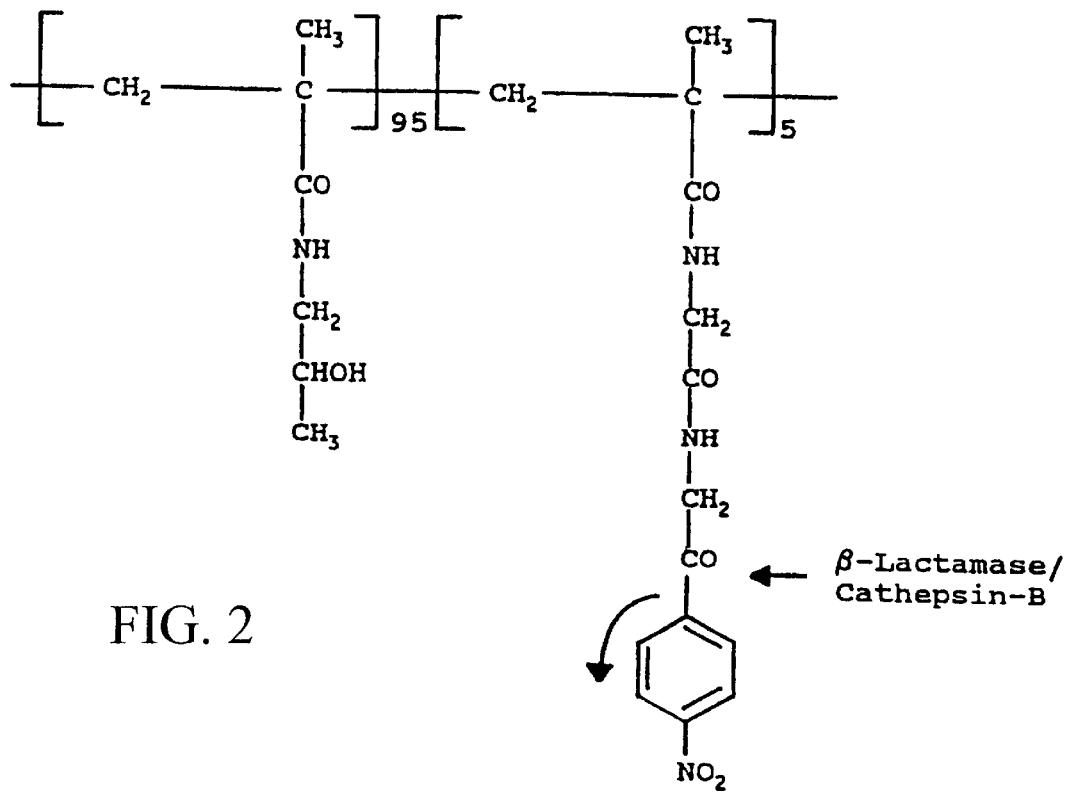
FIG. 2 shows the reactions of Examples 1 and 2.

The invention is further illustrated in the following Examples, with reference to FIGS. 2 etc. of the accompanying drawings.

EXAMPLE 1

HPMA-β-Lactamase Conjugate

β-Lactamase (Sigma; ~28kDa) was attached to the polymeric carrier N-(2-hydroxypropyl)methacrylamide-Glycine-Glycine-p-nitrophenol (HPMA-Gly-Gly-ONp; Polymer Laboratories; ~30kDa) via the nonspecific aminolytic reaction of the ONp groups at controlled pH. The reaction is shown in FIG. 2. The following steps were conducted:

The polymer bearing in the side-chain p-nitrophenol (ONp) groups was dissolved in double-distilled water (4 mg/ml), and this β-lactamase was dissolved in 0.05M phosphate buffer, pH 7.2 (2 mg/ml), and this solution was added to the polymer solution at 4° C. under stirring.

The reaction mixture was stirred in the dark at pH 7.2 for 30 min. The pH was carefully raised over 4 h by adding saturated sodium tetraborate buffer up to pH 8.5 (to prevent enzyme denaturation), and the reaction mixture stirred for another 4 h. The reaction was finished by adding 1-amino-2-propanol (½ the equivalent related to the original ONp groups), to remove unreacted ONp groups. The solution was acidified to pH 7.2.

To remove free polymer and free enzyme, the conjugate was purified by Spectra/POR®CE (Cellulose Ester) sterile DispoDialyzer MW cut-off 50 kDa for separation.

Figure 3:
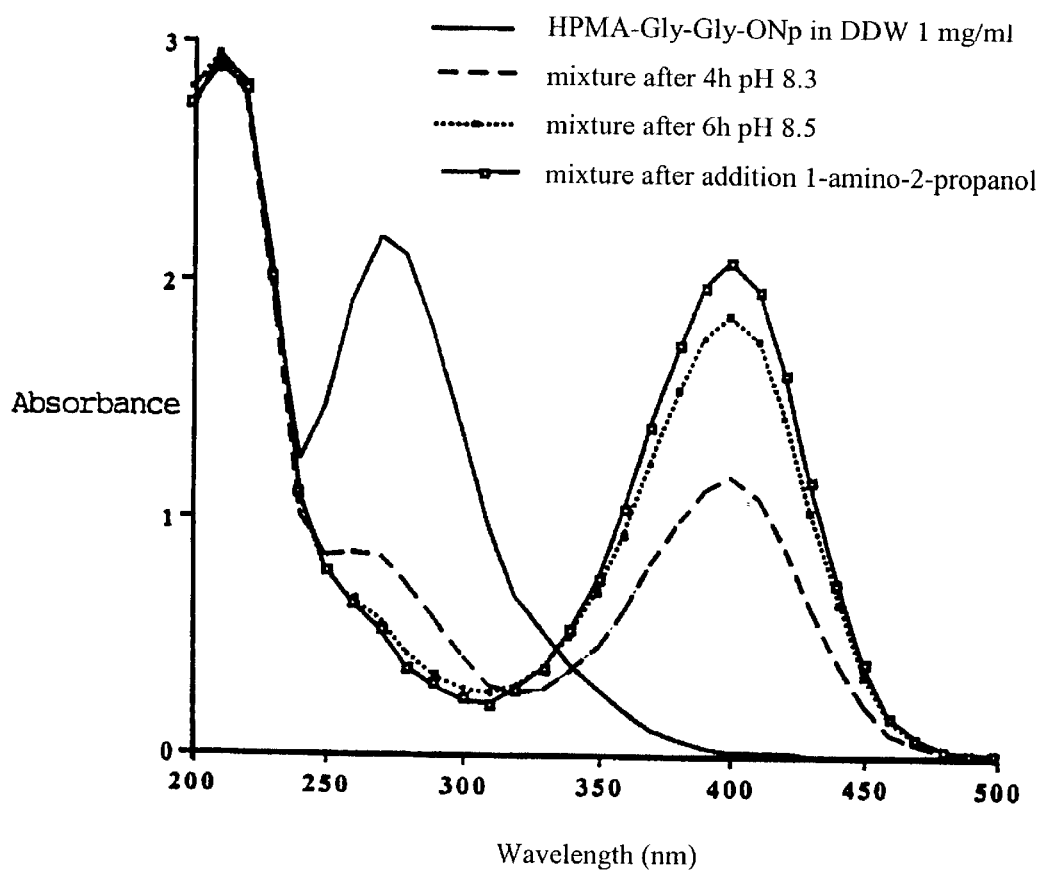
FIG. 3 is a graph showing spectra following the reaction mixture of HPMA-Gly-Gly-ONp and β-lactamase.

The conjugation reaction was followed by UV spectrophotometry, showing the release of p-nitrophenol groups from the HPMA-copolymer. ONp bound to HPMA absorbs at λmax 270 nm while free ONp absorbs at 400 nm. The spectra are shown in FIG. 3.

Proteins reduce alkaline Cu(II) to Cu(I) in a concentration-dependent manner. Bicinchoninic acid is a highly specific chromogenic reagent for Cu(I), forming a purple complex with an absorbance maximum at 562 nm. The absorbance is directly proportional to protein concentration.

The results of the bicinchoninic assay are shown in the following table:

| BSA µg per 20 µl | BSA mean abs | BSA ± SD | beta-lactamase µg/20 µl | beta lactamase mean abs | beta-lactamase ± SD | conjug. µg per 20 µl | conjug. mean abs | conjug. |
|---|---|---|---|---|---|---|---|---|
| 0 | 0 | 0 | 80 | 0.252 | 0.011 | 4.113 | 0.0293 | 0.0037 |
| 2 | 0.05 | 0.003 | 40 | 0.146 | 0.004 | 43.774 | 0.1486 | 0.0049 |
| 4 | 0.1 | 0.002 | 20 | 0.853 | 0.002 | | | |
| 8 | 0.17 | 0.018 | 10 | 0.045 | 0.001 | | | |

-continued

| BSA µg per 20 µl | BSA mean abs | BSA ± SD | beta-lactamase µg/20 µl | beta lactamase mean abs | beta-lactamase ± SD | conjug. µg per 20 µl | conjug. mean abs | conjug. |
|---|---|---|---|---|---|---|---|---|
| 12 | 0.23 | 0.03 | 6.67 | 0.033 | 0.002 | | | |
| 16 | 0.31 | 0.032 | 5 | 0.028 | 0.003 | | | |
| 20 | 0.37 | 0.004 | | | | | | |
| 24 | 0.45 | 0.042 | | | | | | |

4.1 µg beta-lactamase in 20 µl sample of conjugate after separation >50 kDa (0.21 mg/ml).
43.8 µg beta-lactamase in 20 µl sample before separation (2.2 mg/ml).

The yield is $(205.7/1000) \times 100 = 20.57\%$

SDS-PAGE was done in order to show that the release of p-nitrophenol groups was due to aminolysis and not hydrolysis by the phosphate buffer. The free β-lactamase was compared to the bound one relating to molecular weight markers. Unreacted HPMA, as expected from a polymer, gave no band. The free β-lactamase gave two bands coincident with a 30 kDa molecular weight marker due to the two types of enzyme present. The HPMA copolymer-β-lactamase conjugate gave a band corresponding to 60 kDa; after purification, no free enzyme was detected.

In an enzyme activity assay, 10 units/ml β-lactamase (free or conjugated) in phosphate buffer (0.1M, pH 7.0) were added to benzylpenicillin solution (1 mM) and the decreasing UV absorbance at 240 nm was followed with time.

Figure 4:
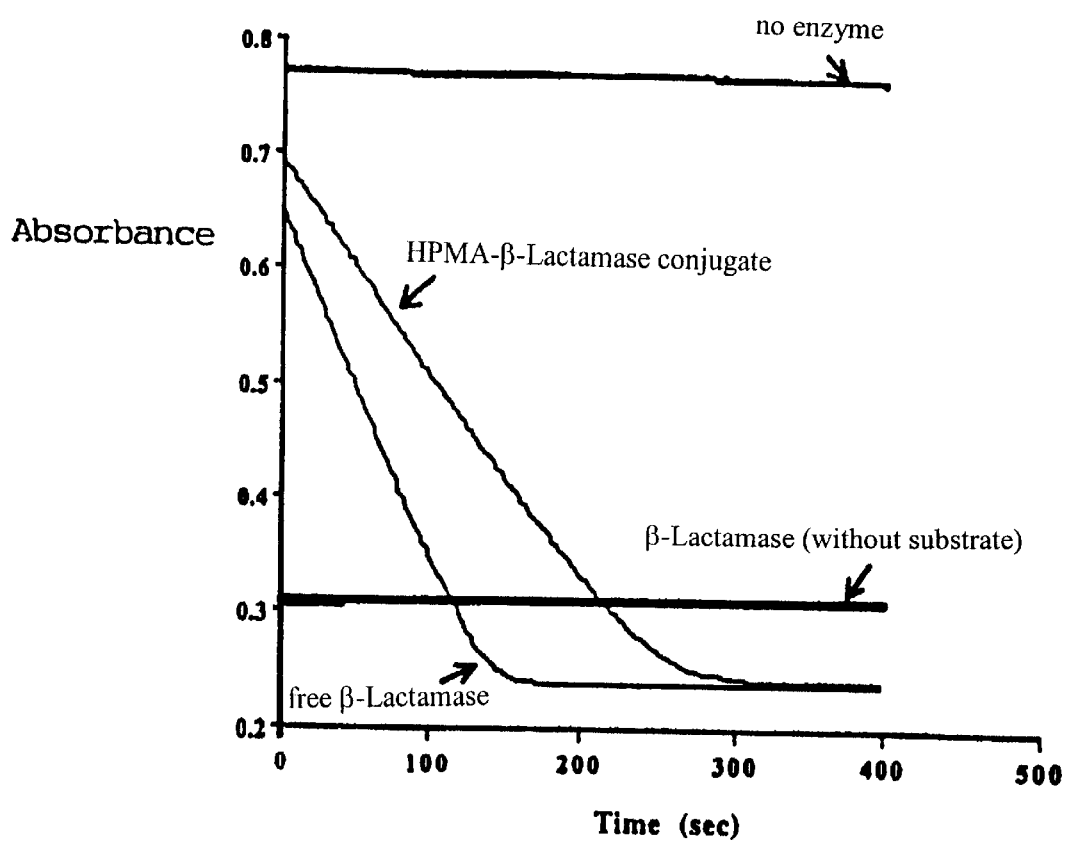
FIG. 4 is a graph showing the degradation of benzylpenicillin by β-lactamase and by HPMA-β-lactamase conjugate.

The activity assay was done using the same amount of enzyme in the free enzyme activity test and in the conjugated enzyme activity test, i.e. 10 units per ml. The activity was tested on free benzylpenicillin as a representative substrate. Results showed that the β-lactamase retained enzyme activity after polymer conjugation; although reduced, it was active enough to cleave the spacer in the final form of PDEPT. The results are shown in FIG. 4.

Michaelis-Menten constants were calculated from the above assays based on the use of free enzyme compared to the conjugated one, in constant concentration (10 units/ml), on different concentrations of benzylpenicillin (1.0 mM, 0.9 mM, 0.75 mM, 0.5 mM, 0.33 mM). The change in absorbance was calculated over time until reaching a plateau. The linear part of the degradation of the different substrate concentrations was plotted and from the slope Vo was calculated and the Lineweaver-Burk graph was plotted.

For the free β-lactamase, Vmax is 0.77 nM/s/unit and Km is 0.22. For the conjugate, Vmax is 0.20 nM/s/unit and Km is 0.07.

The conjugate of Example 1 is suitable for use in combination with a suitable prodrug.

The in vivo biodistribution of HPMA copolymer-enzyme compounds was tested in animal experiments conducted according to the UKCCCR (United Kingdom Co-ordinating Committee on Cancer Research) Guidelines. A B16F10 murine melanoma s.c. model was used.

Male C57BL/6J mice were inoculated with $10^5$ viable B16F10 cells subcutaneously (s.c.). The tumour was allowed to establish until the area was approximately 50–70 mm$^2$ as measured by the product of two orthogonal diameters. $1 \times 10^6$ counts were diluted into 0.5 ml in 0.9% NaCl. The pH was then neutralised with saturated NaOH and the final volume was then made up to 1.0 ml. Of this sample, 100 µl were withdrawn using a 1 ml syringe and 12 gauge needle and counted as a measure of injected dose.

Figure 5:
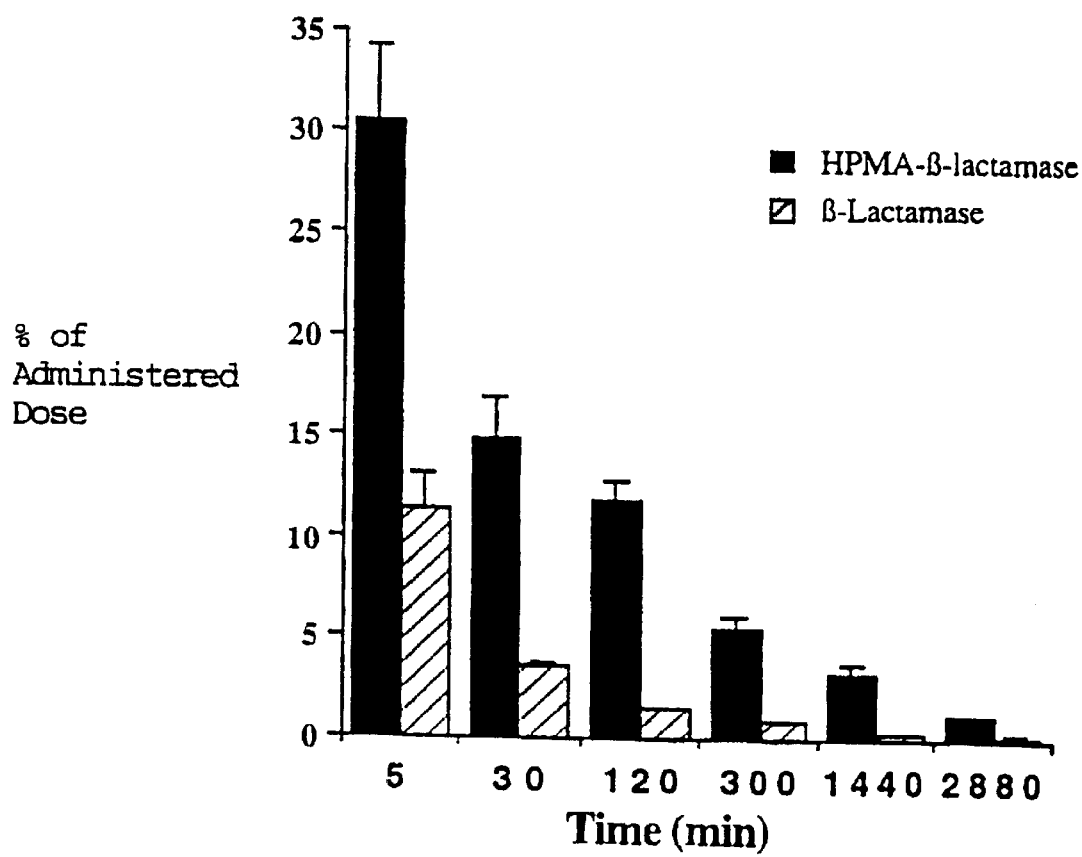
FIG. 5 is a bar chart showing free and conjugated radiolabelled β-lactamase in blood of C57 mice bearing B16F10 melanoma.
Figure 6:
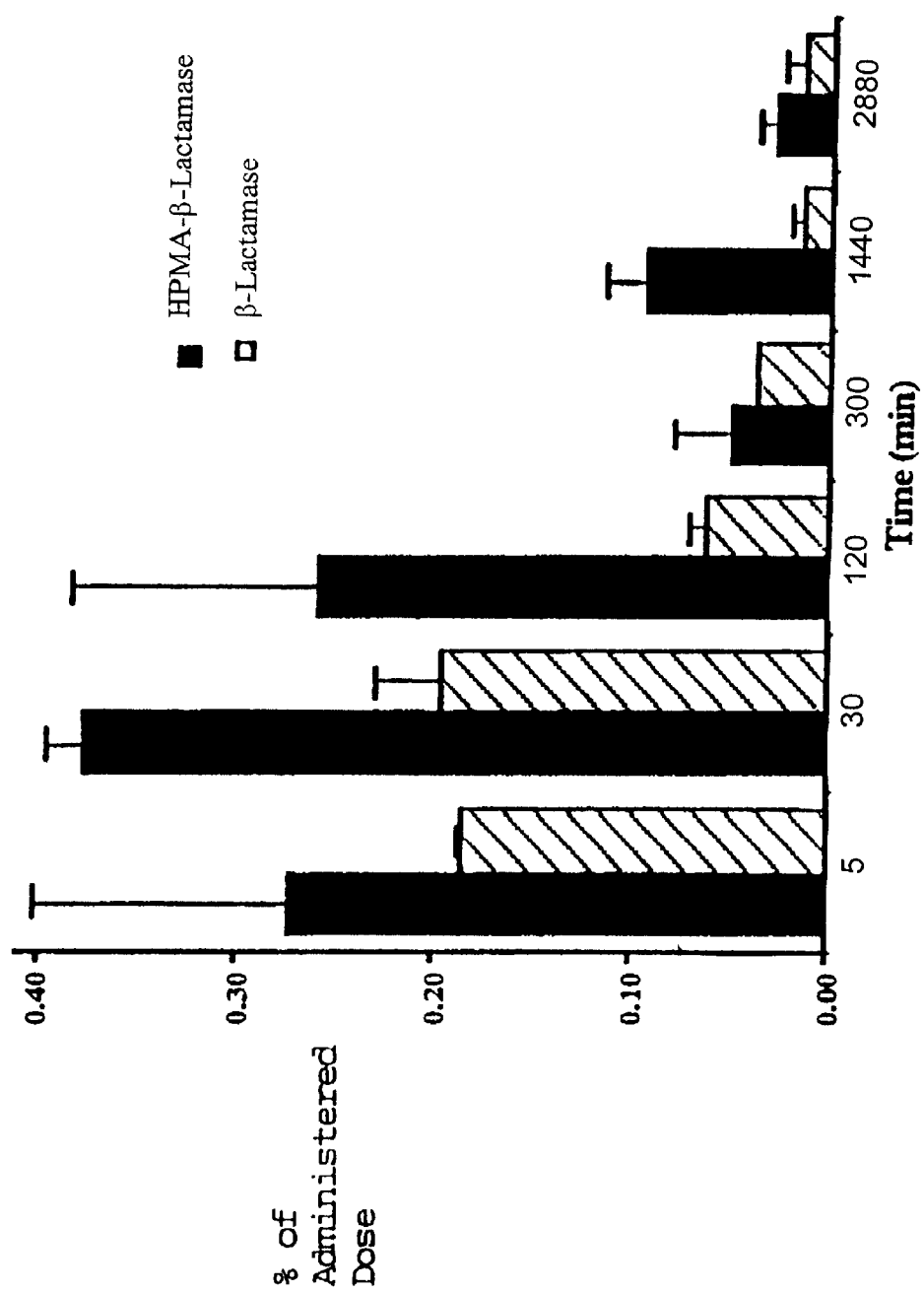
FIG. 6 is a bar chart showing tumour accumulation of free and conjugated radiolabelled β-lactamase in C57 mice bearing B16F10 melanoma.

100 µl ($5 \times 10^5$ CPM) of free or conjugated β-lactamase were injected into the tail vein of C57BL/6J mice (3 replicates per time point). The mice were then placed in a metabolism cage and sacrificed at different time points up to 48 hours. The following tissue samples were dissected: tumour, liver, kidneys, lung, heart, spleen and faeces, urine and blood were collected. Samples were weighed and homogenised in PBS. Samples (1 ml) were then counted in a λ-counter in replicates of 3 (three samples per organ per mouse). The results were then expressed as % dose injected for each organ or % dose recovered for each organ. The blood volume of the mouse was calculated assuming 5.6 ml blood/100 g mouse. The results are shown in FIGS. 5 and 6.

EXAMPLE 2

HPHA-Cathepsin B Conjugate

Cathepsin-B (Sigma; ~28 kDa) was attached to the polymeric carrier (HPMA-Gly-Gly-ONp; ~30 kDa) via the non-specific aminolytic reaction of the ONp groups at controlled pH. The reaction is shown in FIG. 2. The same steps were conducted as in Example 1, except that the polymer was dissolved in double-distilled water at 1 mg/ml and cathepsin-B was used instead of β-lactamase.

The conjugation reaction was again followed by UV spectrophotometry.

The free cathepsin-B was compared to the bound one relating to molecular weight markers, by SDS-PAGE. Unreacted HPMA, as expected from a polymer, gave no band. The free cathepsin-B gave bands coincident with 30 kDa and 90 kDa molecular weight marker due to the different chains of enzyme present. The HPMA copolymer-cathepsin-B conjugate gave a band corresponding to 60 kDa and 97 kDa (due to cross-linking). After purification no free enzyme was detected.

Activity of free or conjugated cathepsin-B was assayed by measuring the release of p-nitroaniline (NAp) at 410 nm from the tripeptide Bz-Phe-Val-Arg-NAp during incubation at 37° C. in citrate buffer (0.2 M, pH 5.5) containing EDTA (10 mM) and reduced glutathione (50 mM).

Figure 7:
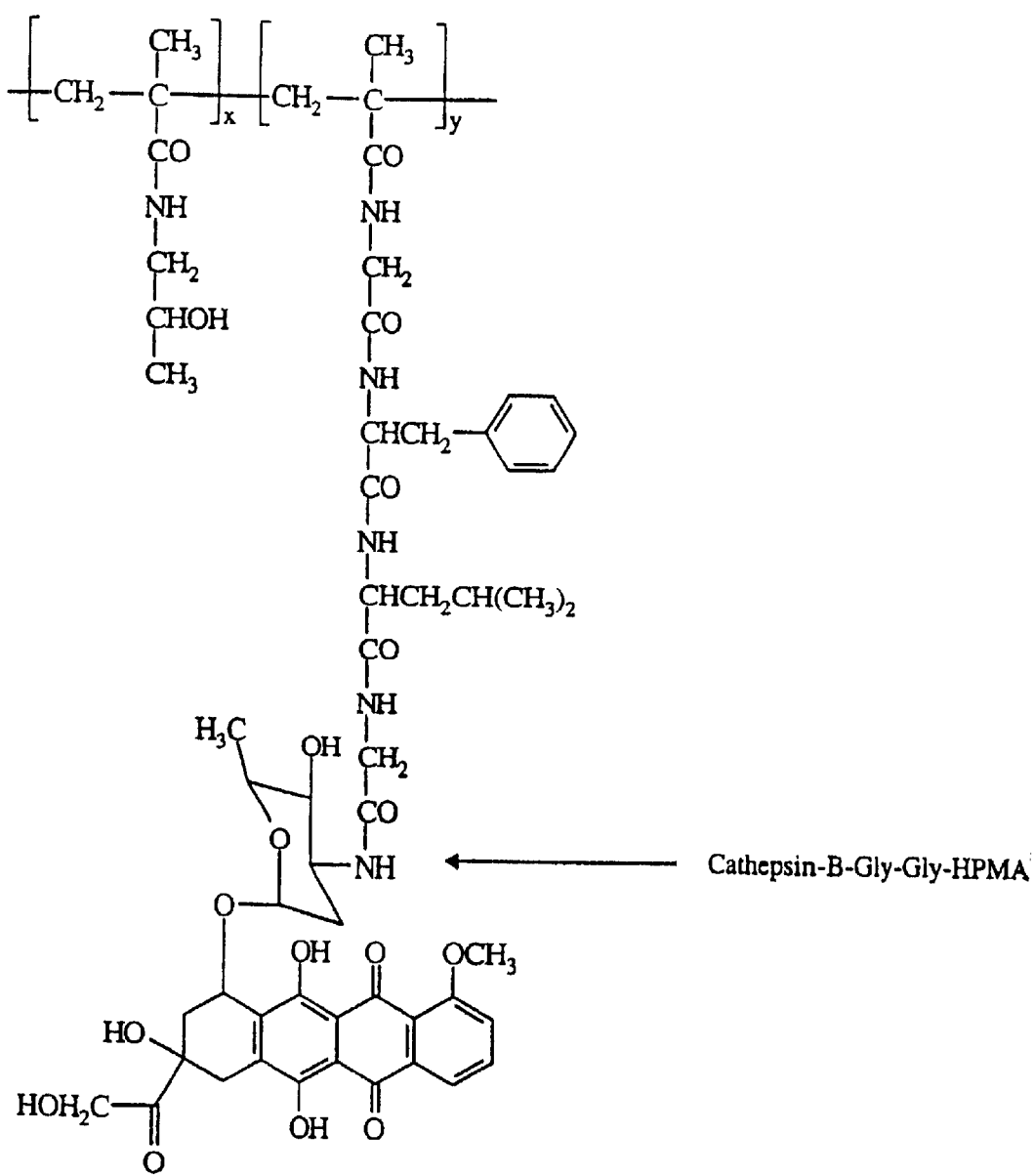
FIG. 7 shows the structure of the prodrug PK1, cleavable by cathepsin B.

The cathepsin-B conjugate of Example 2 is suitable for use in combination with a suitable prodrug such as HPMA-Gly-Phe-Leu-Gly-doxorubicin (PK1; see FIG. 7).

Figure 8:
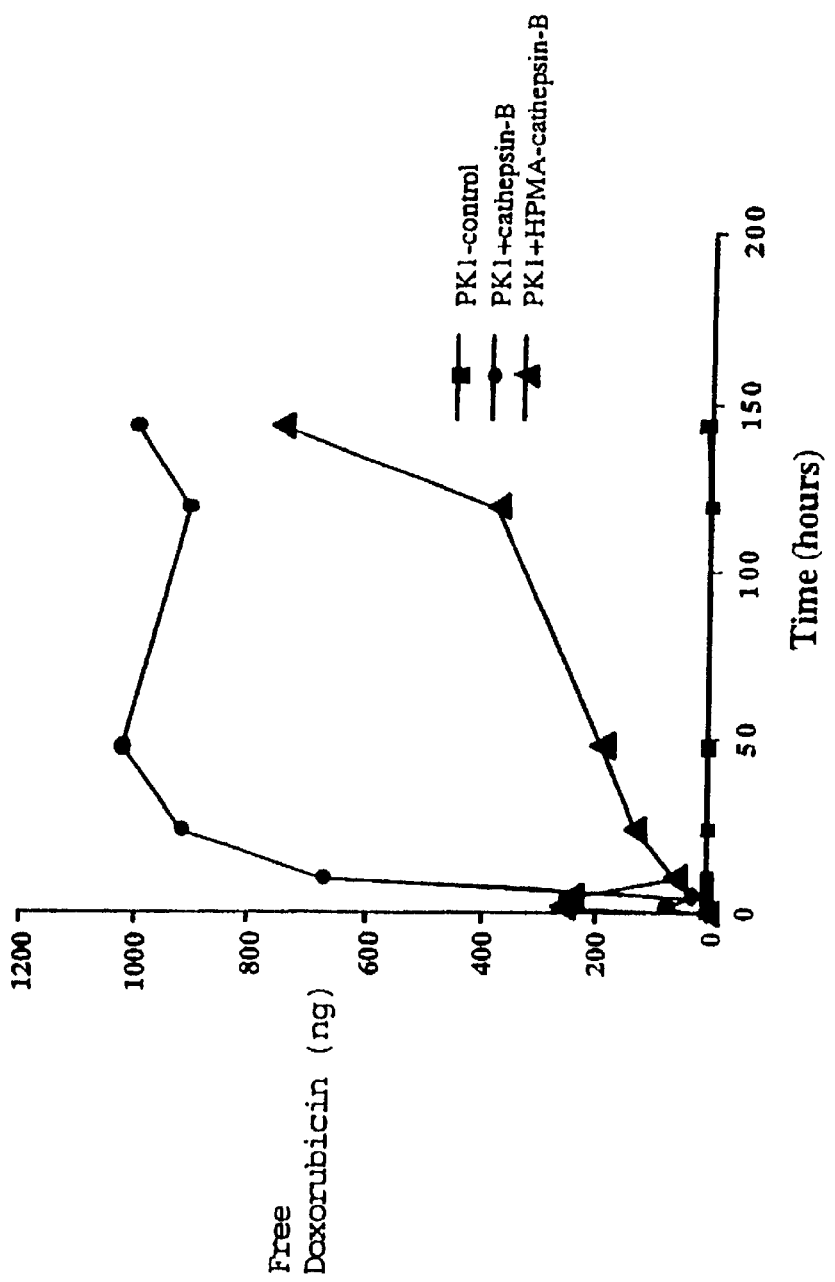
FIG. 8 is a graph showing the release of doxorubicin from HPMA-Gly-Phe-Leu-Gly-dox by free and conjugated cathepsin-B and without.

The activity of cathepsin-B (free or conjugated) on the high molecular weight substrate PK1 was assessed by HPLC. Incubation of PK1 with cathepsin-B was carried out at 37° C. in a final volume of 1 ml consisting of 400 µl 1 mg/ml of PK1 in citrate buffer (pH 5.5, 0.2 M), 100 µl EDTA solution in buffer (10 mM), 100 µl reduced glutathione (GSH 50 mM) and 400 µl HPMA-cathepsin-B or free cathepsin-B in buffer (equivalent to cathepsin-B concentration present in the conjugate-1 mg/ml). Tubes containing PK1 without enzymes were also prepared, to assess the levels of hydrolysis, as controls. 100 µl samples were taken at various times, immediately frozen in liquid nitrogen and stored frozen in the dark until processed by HPLC. Then the samples were mixed with 100 ng daunomycin (DNM), as an internal standard, ammonium formate buffer (pH 8.5 and extraction mixture (chloroform:propan-2-ol). Tubes were centrifuged, the aqueous layer was carefully removed and the organic fraction evaporated to dryness using the Techne nitrogen system operated at no more than 13.8 kPa (2 lbf/in$^2$) of N$_2$(g). Evaporated samples were redissolved in methanol prior to analysis. The release of free doxorubicin from PK1 in vitro is shown in FIG. 8.

Figure 9:
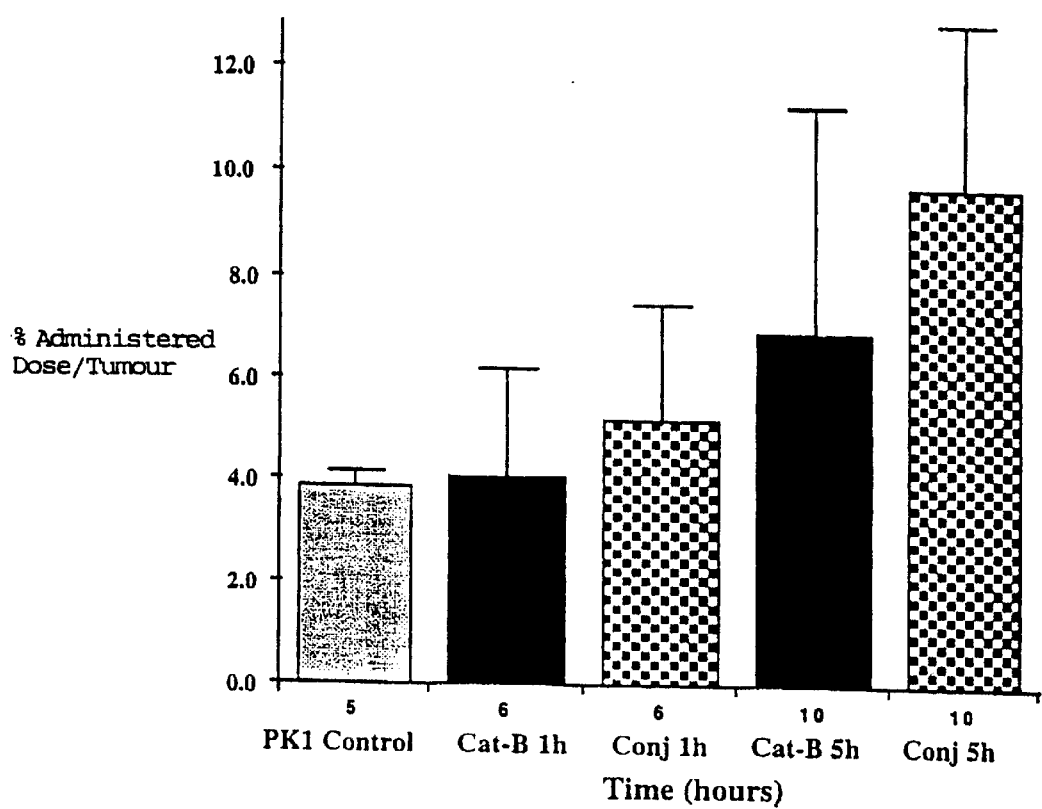
FIG. 9 is a bar chart showing the release of doxorubicin from PK1 in C57 mice bearing B16F10 melanoma by free and conjugated cathepsin-B.
Figure 10:
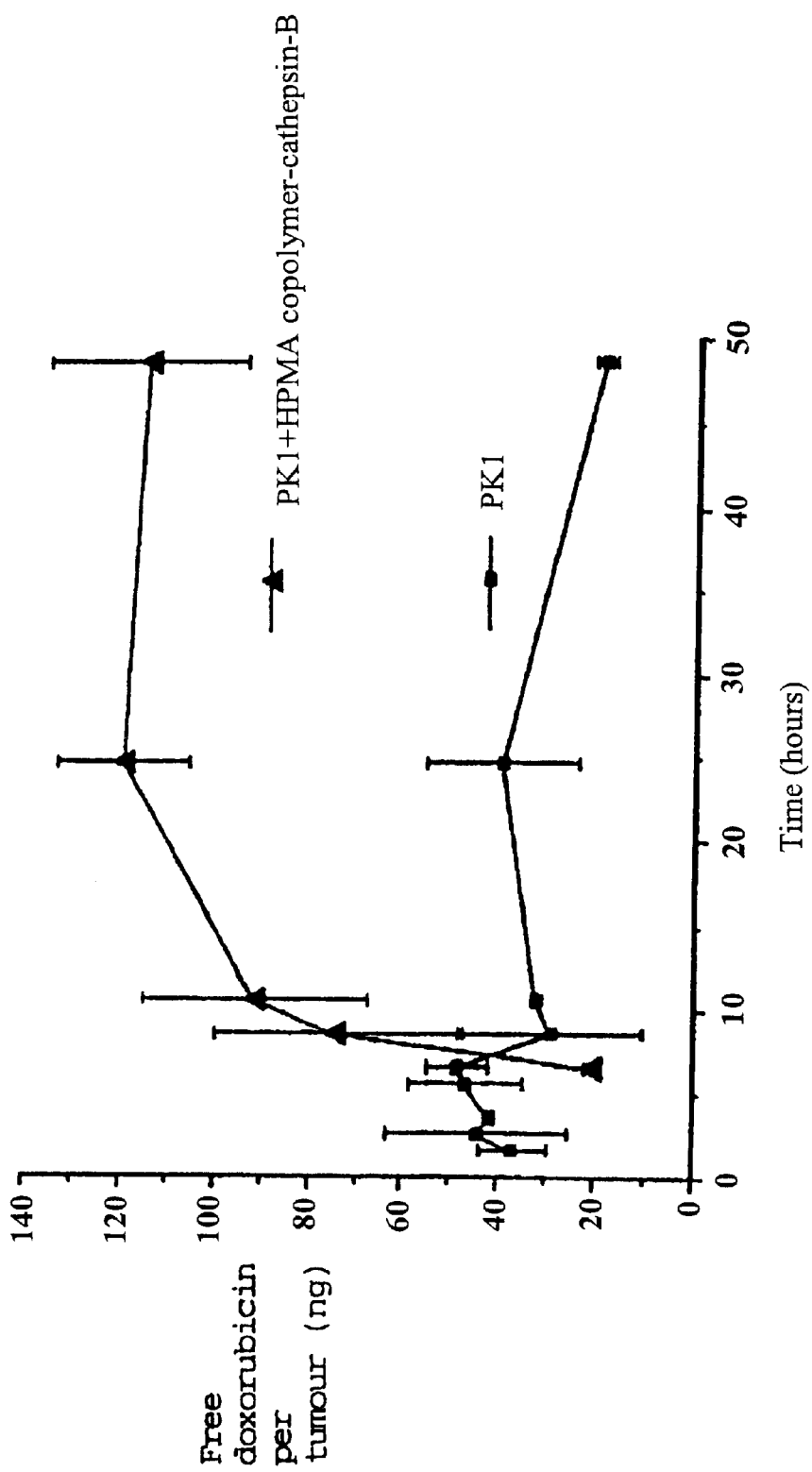
FIG. 10 is a graph showing doxorubicin release from PK1 after IV administration of HPMA copolymer-cathepsin-B to C57 black male mice bearing B16F10 murine melanoma.

Evaluation in vivo was conducted using the B16F10 murine melanoma model. Male C57BL/6J mice were inoculated with 10 viable B16F10 cells subcutaneously (s.c.). The tumour was allowed to establish until the area was approximately 50–70 mm$^2$ as measured by the product of two orthogonal diameters. Animals were injected i.v. with PK1 (5 mg/kg and 10 mg/kg equivalent of doxorubicin) or PK1 (5 mg/kg and 10 mg/kg equivalent of doxorubicin) followed after 5 hours by free cathepsin-B (3.63 mg/kg) or HPMA-copolymer-Gly-Gly-cathepsin-B (3.63 mg/kg equivalent of cathepsin-B) and sacrificed at different time points up to 48 hours. The following tissue samples were dissected: tumour, liver, kidneys, lung, heart, spleen and urine and blood were collected. Samples were weighed, homogenised in PBS, and mixed with 100 ng daunomycin (DNM), as an internal standard, ammonium formate buffer (pH 8/5) and extraction mixture (chloroform:propan-2-ol). Tubes were centrifuged, the aqueous layer was carefully removed and the organic fraction evaporated to dryness using the Techne nitrogen system operated at no more than 13.8 kPa (2 lbf/in$^2$) of N$_2$(g). Evaporated samples were redissolved in methanol prior to HPLC analysis. The results, comparing the release of doxorubicin from the polymer conjugate with and without the enzyme, are shown in FIGS. 9 and 10.

References

1. Bagshawe, Br. J. Cancer 56:531–532 (1987).
2. Senter, The FASEB Journal 4:188–193 (1990).
3. Ram et al, Cancer Res. 53:83–88 (1993).
4. Knox and Connors, Clinical Immunotherapy 3:136–153 (1995).
5. Melton et al, Drugs of The Future 21(2):167–181 (1996).
6. Bagshawe and Begent, Advanced Drug Delivery Reviews, 22:365–367 (1996).
7. Duncan et al, S. T. P. Pharma Sci. 6(4):237–263 (1996).
8. Maeda and Matsumura, CRC Critical Rev. Therap. Drug Carrier Sys. 6:193-210 (1989).
9. Rihova and Kopecek, J. Controlled Rel. 2:289–310 (1985).
10. Flanagan et al, J. Bioactive and Compatible Polymers 5:151–166 (1990).
11. Seymor et al, Eur. J. Cancer (May 1995).
12. Maeda et al, Bioconj. Chem. 3:351–362 (1992).
13. Takakura and Hashida, Crit. Rev. Onco. Hematol. 18:207–231 (1995).
14. Svensson et al, Bioconjug. Chem. 3:176–181 (1992).
15. Senter et al, Bioconjug. Chem. 6:389–394 (1995).
16. Seymor et al, Brit. J. Cancer, 70:636–641 (1994).
17. Duncan et al, J. Controlled Rel. 3:175–210 (1992).

What is claimed is:

1. A product comprising, as a combined preparation for sequential administration in drug treatment, an enzyme conjugate and a prodrug, the enzyme conjugate consisting of a functional enzyme covalently bound to a polymeric carrier, and the prodrug being substantially inactive in terms of drug activity but capable of being activated by the enzyme.

2. The product according to claim 1, wherein the prodrug comprises a carrier to which the drug is covalently conjugated.

3. The product according to claim 2, wherein the carrier of the prodrug is a polymer.

4. The product according to claim 3, wherein the enzyme is a protease and the drug is conjugated to the polymeric carrier by a peptidyl linker which is cleavable by a protease enzyme.

5. The product according to claim 1, wherein the enzyme is a thiol-dependent protease.

6. The product according to claim 5, wherein the thiol-dependent protease is cathepsin-B.

7. The product according to claim 6, wherein the carrier of the prodrug is a polymer.

8. The product according to claim 1, wherein the enzyme is β-lactamase.

9. The product according to claim 1, wherein the polymeric carrier comprises a polymer or copolymer of a hydroxyalkyl (meth)acrylamide.

10. The product according to claim 9, wherein the hydroxyalkyl (meth)acrylamide is hydroxypropyl methacrylamide.

11. A product comprising, as a combined preparation for sequential administration in drug treatment, an enzyme conjugate and a prodrug, the enzyme conjugate consisting of a functional enzyme covalently bound to a polymeric carrier, and the prodrug comprising a drug bound to a polymeric carrier by a peptide linker which is cleavable by the enzyme.

12. The product according to claim 11, wherein the enzyme conjugate comprises an antibody to which the enzyme is covalently conjugated.

13. The product according to claim 11, wherein the enzyme is a thiol-dependent protease.

14. The product according to claim 11, wherein the polymeric carrier comprises a polymer or copolymer of a hydroxyalkyl (meth)acrylamide.

15. The product according to claim 14, wherein the hydroxyalkyl (meth)acrylamide is hydroxypropyl methacrylamide.

16. The product according to claim 11, wherein the enzyme is a β-lactamase.

17. A product comprising, as a combined preparation for sequential administration in drug treatment, an enzyme conjugate and a prodrug, the enzyme conjugate consisting of a functional thiol-dependent protease covalently bound to a polymeric carrier, and the prodrug comprising a drug bound to a carrier by a peptide linker which is a substrate for the thiol-dependent protease.

18. The product according to claim 17, wherein the carrier of the prodrug is a polymer.

19. The product according to claim 17, wherein the thiol-dependent protease is cathepsin-B.

20. The product according to claim 17, wherein the polymeric carrier comprises a polymer or copolymer of a hydroxyalkyl (meth)acrylamide.

21. The product according to claim 20, wherein the hydroxyalkyl (meth)acrylamide is hydroxypropyl methacrylamide.

22. A conjugate which consists of a functional thiol-dependent protease covalently bound to a polymeric carrier.

23. The conjugate according to claim 22, wherein the protease is cathepsin-B.

24. The conjugate according to claim 22, for use in therapy.

25. The conjugate according to claim 22, wherein the polymer is a hydroxyalkyl (meth)acrylamide.

26. The conjugate according to claim 25, wherein the hydroxyalkyl (meth)acrylamide is hydroxypropyl methacrylamide.

27. A pharmaceutical composition comprising a pharmaceutically-acceptable excipient and a conjugate which consists of a functional thiol-dependent protease covalently bound to a polymeric carrier.

28. The pharmaceutical composition according to claim 27, wherein the protease is cathepsin-B.

29. A method of providing a therapeutic treatment that is associated with an active drug to a person or animal in need of such treatment, said method comprising the separate administration of an enzyme conjugate that releases said active drug from a prodrug, the enzyme conjugate consisting of a functional enzyme covalently bound to a polymeric carrier, and the prodrug being substantially inactive in terms of drug activity but capable of being activated by the enzyme.

30. The method according to claim 29, wherein the prodrug is administered before the enzyme conjugate.

31. The method according to claim 29, wherein the polymeric carrier comprises a polymer or copolymer of a hydroxyalkyl (meth)acrylamide.

32. The method according to claim 29, wherein said hydroxyalkyl (meth)acrylamide is hydroxypropyl methacrylamide.

33. The method according to claim 29, wherein the enzyme is a protease.

34. The method according to claim 29, wherein the enzyme is a thiol-dependent protease.

35. The method according to claim 34, wherein the thiol-dependent protease is cathepsin-B.

36. The method according to claim 29, wherein the enzyme is β-lactamase.

37. The method according to claim 29, wherein the prodrug comprises a carrier to which the drug is covalently conjugated.

38. The method according to claim 37, wherein the carrier of the prodrug is a polymer.

39. The method according to claim 38, wherein the drug is conjugated to the polymeric carrier by a peptidyl linker which is cleavable by a protease enzyme.

* * * * *